# United States Patent [19]

Neward

[11] 4,254,764
[45] Mar. 10, 1981

[54] CLIP ELECTRODE

[76] Inventor: Theodore C. Neward, P.O. Box 725, Cucamonga, Calif. 91730

[21] Appl. No.: 16,427

[22] Filed: Mar. 1, 1979

Related U.S. Application Data

[63] Continuation-in-part of Ser. No. 917,556, Jun. 21, 1978, abandoned.

[51] Int. Cl.³ ............................................. A61B 5/04
[52] U.S. Cl. .................................................. 128/642
[58] Field of Search ............... 128/642, 639, 784–788, 128/802, 419 P, 794

[56] References Cited

U.S. PATENT DOCUMENTS

| | | | |
|---|---|---|---|
| Re. 28,990 | 10/1976 | Hon et al. | 128/642 |
| 569,380 | 10/1896 | Hollingsworth | 128/787 X |
| 1,644,803 | 10/1927 | Wappler | 128/802 |
| 1,723,602 | 8/1929 | Catlin | 128/794 |
| 2,831,174 | 4/1958 | Hilmo | 128/639 |
| 3,029,820 | 4/1962 | Franklin | 128/640 |
| 3,067,749 | 12/1962 | Walters | 128/639 |
| 3,087,486 | 4/1963 | Kilpatrick | 128/642 |
| 3,120,227 | 2/1964 | Hunter, Jr. et al. | 128/642 |
| 3,326,207 | 6/1967 | Egan | 128/642 |
| 3,416,534 | 12/1968 | Quinn | 128/785 |
| 3,472,234 | 10/1969 | Tachick | 128/785 |
| 3,580,242 | 5/1971 | LaCroix | 128/642 |
| 3,750,650 | 8/1973 | Ruttgers | 128/642 |
| 3,800,784 | 4/1974 | Kiszel et al. | 128/642 |
| 3,835,864 | 9/1974 | Rasor et al. | 128/785 |
| 3,890,420 | 6/1975 | Neward | 264/261 |
| 3,989,038 | 11/1976 | Neward | 128/642 |
| 3,999,555 | 12/1976 | Rerson | 128/785 |
| 4,011,875 | 3/1977 | Lehr et al. | 128/785 |
| 4,080,961 | 3/1978 | Eaton | 128/642 |

FOREIGN PATENT DOCUMENTS

| | | | |
|---|---|---|---|
| 2133304 | 3/1977 | Fed. Rep. of Germany | 128/785 |
| 2162777 | 7/1973 | France | 128/642 |
| 1316072 | 5/1973 | United Kingdom | 128/642 |
| 1457426 | 12/1976 | United Kingdom | 128/642 |
| 572262 | 9/1977 | U.S.S.R. | 128/642 |

OTHER PUBLICATIONS

Copland et al., "A Simple Cinicel Skin Electrode", Lancet, No. 7330, vol. 1, p. 416, Feb. 1964.
Hon, "The Instrumentation . . . Fetal Electrocardiography", Conn. Med., May, 1960, vol. 24, No. 5, p. 289.
Junge, "A New Technique . . . During Birth", Obs. & Gyn, Feb. 1969, pp. 129–133.

Primary Examiner—Lee S. Cohen
Attorney, Agent, or Firm—Lyon & Lyon

[57] ABSTRACT

An electrode and carrier assembly is disclosed for attachment to a biological subject, such as a fetus during labor and delivery to monitor the fetal heart rate. The electrode structure includes a clip-like body having clamping portions and members adapted to engage cam surfaces within a carrier. While the electrode structure is housed within the carrier the clamping portions are held apart. Attachment is accomplished by placing the carrier against the subject and moving the members into engagement with the cam surfaces, whereby the cam surfaces eject the electrode structure from the carrier by the cam action thus allowing the clamping portions thereof to clamp onto the subject's skin. The carrier may then be removed completely, leaving only the electrode structure with its associated wiring.

9 Claims, 10 Drawing Figures

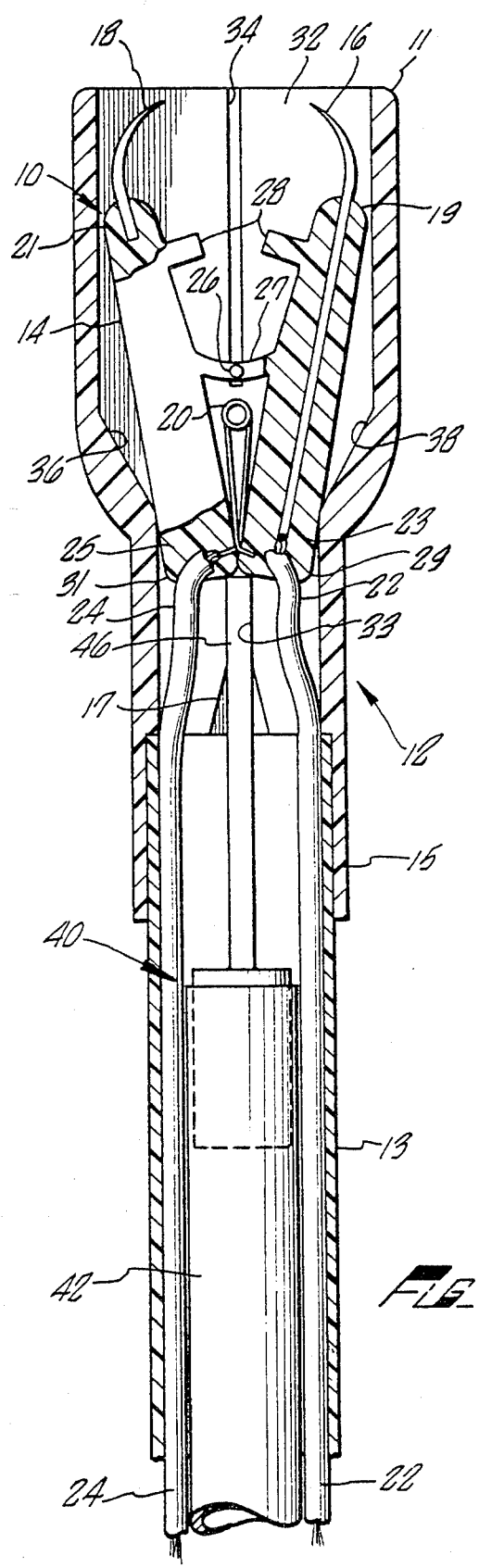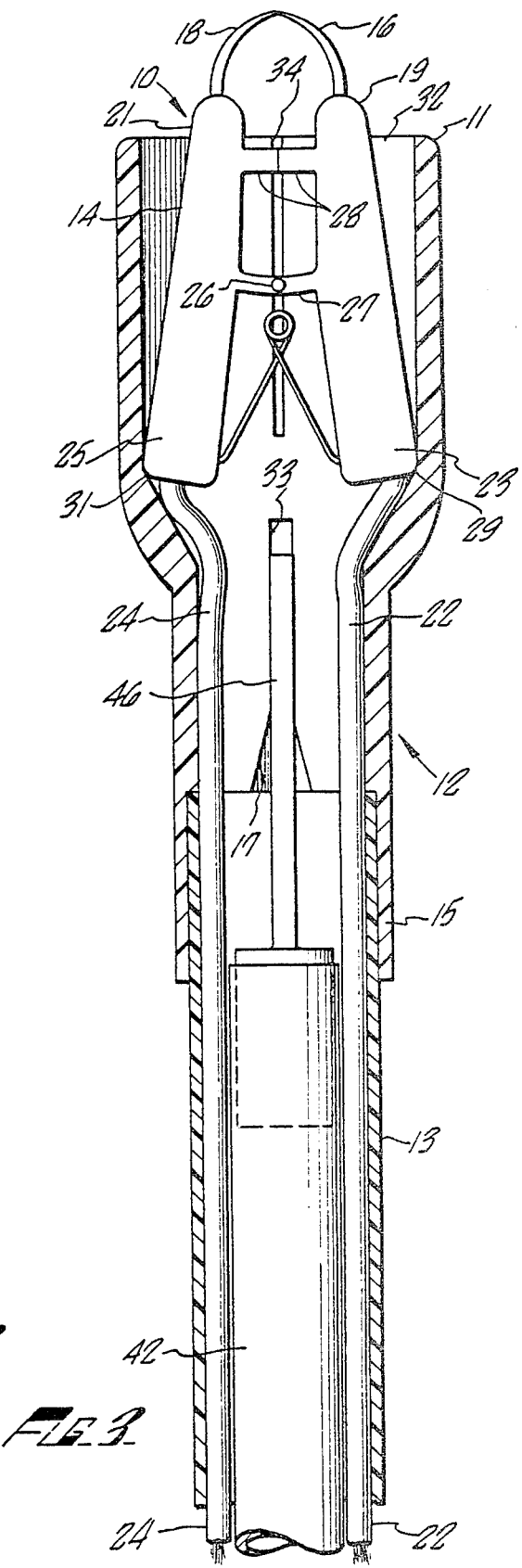
FIG. 2.
FIG. 3.

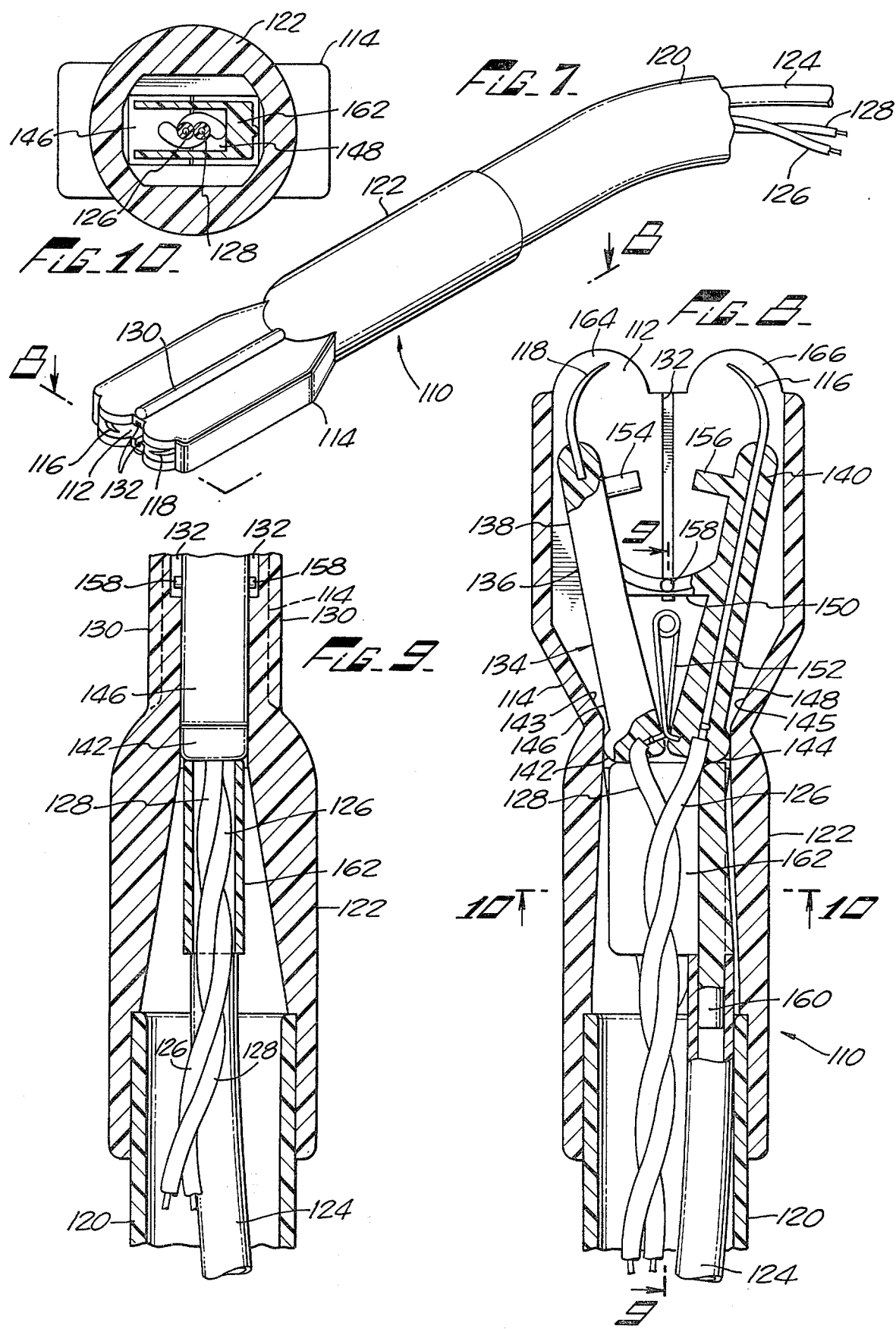

CLIP ELECTRODE

BACKGROUND OF THE INVENTION

The present application is a continuation-in-part of application Ser. No. 917,556, filed June 21, 1978, now abandoned.

The present invention relates to electrodes, and more particularly to an electrode, and carrier therefor, suitable for attachment to a fetus during labor and delivery to monitor the fetal heart rate.

It is desirable to monitor the fetal heart rate continuously during labor and delivery in order to obtain an immediate indication of the presence of undue distress or danger to the fetus. Devices attached external to the mother's body have proven inadequate for this purpose because they do not clearly distinguish the fetal heart rate from that of the mother. Therefore, various devices have been developed for attachment directly to the fetus during labor.

An early device of this type consisted of a "C" shaped wire, insulated except at the opposed tips thereof, which was inserted into the uterus and attached to the fetal scalp manually or by a forcep. This device was difficult to manipulate and insert, and did not attach securely to the fetus. Later devices were developed that screwed into the skin, such as those disclosed in Hon et al. U.S. Pat. No. Re. 28,990 and Ruttgers U.S. Pat. No. 3,750,650. Tachick U.S. Pat. No. 3,472,234 discloses another screw-type electrode. These devices require a manual attachment technique that is unusual and difficult for a physician to perform.

Other intrauterine fetal monitoring devices have taken various forms. Egan U.S. Pat. No. 3,326,207 discloses a pair of contact electrodes mounted on balloons. LaCroix U.S. Pat. No. 3,580,242 discloses a barbed, fishhook-like electrode inserted by a forcep. Hunter, Jr. et al., U.S. Pat. No. 3,120,227 discloses a spring steel electrode having forcep-like branches that converge sharply to a point. A cylindrical sleeve must remain in the uterus to engage the branches and hold them together, making this device cumbersome to work with.

In Neward U.S. Pat. No. 3,989,038, there is disclosed a clip-like fetal electrode having opposed jaws normally held together by spring tension, mounted on a long tube which may be removed after the electrode is attached to the fetus. Attachment, however, is accomplished by manipulation of one of the jaws through a rachet and cam assembly in a manner which may be awkward for a physician to perform while the electrode is inserted into the uterus. An alternate means for inserting an electrode into a body cavity is disclosed in Kilpatrick U.S. Pat. No. 3,087,486, consisting of a tubular carrier sleeve containing a plunger which is depressed to drive the electrode into the tissue, after which the sleeve may be withdrawn from the body. The insertion sleeve, however, is disclosed in connection with a cardiac electrode, and is therefore quite rigid since it must penetrate the chest wall. A similar rigid penetration tool is disclosed in Quinn U.S. Pat. 3,416,534, but in connection with a helix-shaped cardiac electrode that is screwed into the myocardium and therefore has the same disadvantages as the screw-type electrodes described in the patents mentioned above. Another cardiac electrode in the form of a spiral is disclosed in Rasor et al., U.S. Pat. No. 3,835,864, for intracardiac use as a Pacemaker. A transvenous or transarterial catheter is used for insertion.

SUMMARY OF THE INVENTION

According to the present invention there is provided an electrode and carrier assembly particularly adapted for fetal monitoring. The assembly is easily inserted into the uterus during labor, is operated in a fashion familiar to doctors, attaches easily and safely to the fetus, requires a minimum of associated structure while attached, and may be easily detached from the fetus after delivery.

The electrode structure includes a clip-like body supporting at least one electrode, which may be one of the clamping portions of the clip, and having members adapted to engage cam surfaces within a carrier. Prior to attachment to the fetus the electrode structure is housed in the carrier with the clamping portions held apart. When it is desired to attach the electrode structure to the fetus, the physician inserts the assembly into the uterus until the scalp of the fetus is encountered, and then activates a plunger much like a familiar hypodermic syringe to move the members of the electrode structure into engagement with the cam surfaces of the carrier. The electrode structure is then ejected from the carrier by the cam action, allowing the clamping portions thereof to come together by spring action to penetrate and grasp the fetal epidermis firmly. The carrier may then be removed from the uterus, leaving only the electrode and its associated wires which are then connected to conventional heart rate monitoring equipment.

Accordingly, it is an object of the present invention to provide an improved electrode and carrier assembly.

It is another object of the present invention to provide an improved fetal monitoring electrode.

It is a further object of the present invention to provide a carrier permitting simple insertion and attachment of a fetal electrode.

These and other objects and advantages of the present invention will become apparent from the following detailed description taken in conjunction with the accompanying drawings.

BRIEF DESCRIPTION OF THE DRAWINGS

FIG. 2 is a detailed side view, in cross section, of a portion of the electrode carrier of FIG. 1, showing housed therein an electrode structure according to the present invention in partial cross section in a position suitable for storage prior to use.

FIG. 3 is a side view in cross section of a portion of an electrode carrier as in FIG. 2, showing the electrode structure as it is positioned after being partially ejected from the carrier for attachment to the fetal epidermis.

FIG. 7 is a perspective view of a portion of an electrode carrier according to a presently preferred embodiment of the present invention, showing part of an electrode structure housed therein.

FIG. 8 is a detailed side view, in cross section, of a portion of the electrode carrier of FIG. 7, showing housed therein an electrode structure according to the present invention in partial cross section in a position suitable for storage prior to use.

FIG. 9 is another side cross sectional view of a portion of the electrode carrier of FIG. 7, taken at right angles to the side view of FIG. 8 and showing a portion of an electrode structure and a plunger housed therein as in FIG. 8.

FIG. 10 is an end cross-sectional view of the electrode carrier of FIG. 7, showing detail of the internal shape thereof and the plunger housed therein.

DETAILED DESCRIPTION OF THE INVENTION

Figure 1:
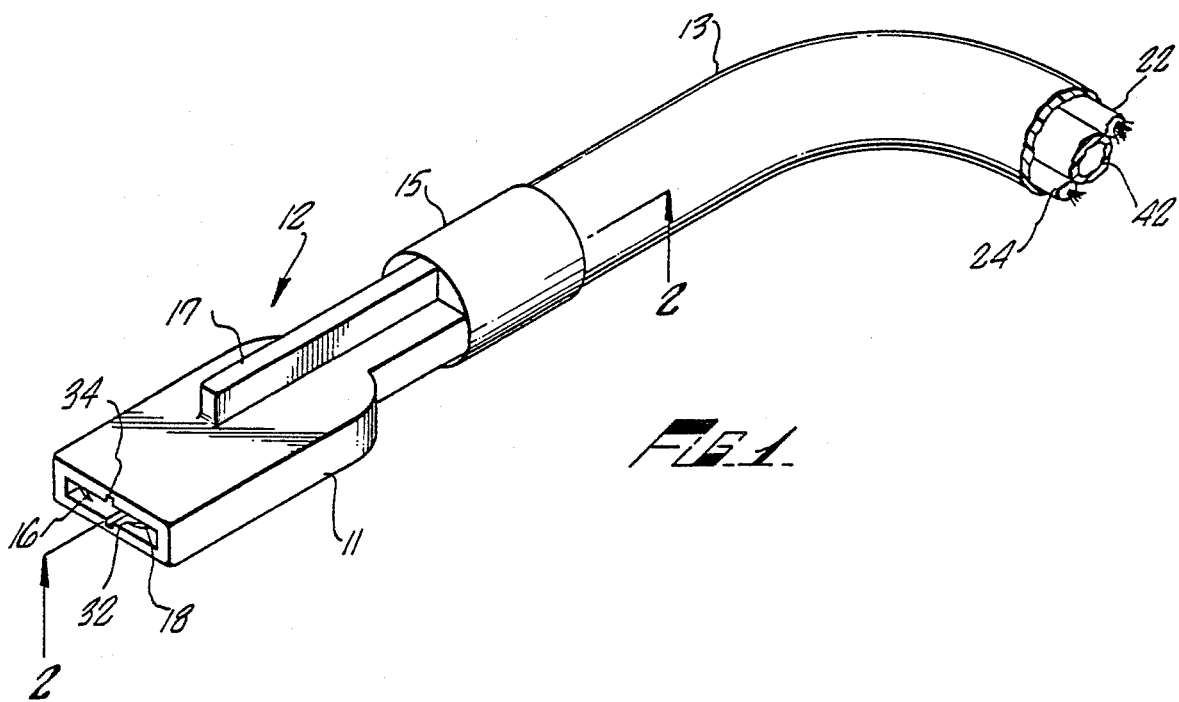
FIG. 1 is a perspective view of a portion of an electrode carrier according to one embodiment of the present invention, showing part of an electrode structure housed therein.

Referring first to FIG. 1, there is illustrated a perspective view of an electrode carrier 12 according to one embodiment of the present invention. Within a cavity 32 of an electrode housing portion 11 of the carrier 12 there is housed an electrode structure to be described in greater detail hereinafter, the tips of whose clamping portions 16 and 18 may be viewed in FIG. 1. The carrier 12 also includes a flexible or curved tube portion 13 extending from a cylindrical connecting member 15 and housing a plunger 40 having a flexible rod portion 42 shown in FIG. 1 and wires 22 and 24, and the electrode housing portion 11 of the carrier 12 includes a raised portion 17 extending from both sides thereof for mating with the connecting member 15 and receiving a portion of the plunger 40, all to be described in greater detail hereinafter.

Referring next to FIG. 2, which is a side view taken along the line 2—2 of FIG. 1, there is illustrated an electrode structure 10 according to the present invention housed within the electrode carrier 12. The electrode structure 10 comprises a clip-type body 14 that may be constructed, for example, of a flexible plastic, having arms 19 and 21 supporting opposed clamping members 16 and 18, respectively, which are preferably metal wires sharpened to a point to easily penetrate the fetal epidermis, and further having legs 23 and 25 joined respectively to the arms 19 and 21, the pairs of arms and legs being connected by a resilient web 27 so that the body 14 possesses roughly the shape of the capital letter "H". A spring 20 which may be, for example, of a coil or compression type is embedded in the legs 23 and 25 of the body 14 to exert an outwardly expansive force on the legs, with the result that the clamping members 16 and 18 are normally urged together or toward the closed position. The member 16 illustrated in this embodiment serves also as a sensing electrode, and is connected through the body 14 to a wire 22 leading to a terminal (not shown) which may be connected to a monitoring unit. Another wire 24 leads from the body 14 and is connected within the body 14 to the spring 20, so that the spring 20 acts as a ground or reference electrode when the electrode structure 10 is surrounded by the maternal fluid present in the uterus prior to childbirth. A pair of guide pegs or pins 26 may be located on opposite sides of the web 27 of the body 14 for engagement with the carrier 12 as will be described in more detail hereinafter. Stops 28 may be provided on the facing surfaces of the arms 19 and 21 to allow the tips of the members 16 and 18 properly to engage each other and to limit the effective range of expansion of the spring 20.

The electrode carrier 12 includes an elongated, flexible or curved cylinder or tube 13 and an electrode housing 11 joined by a cylindrical connecting member 15, as previously discussed in connection with FIG. 1 and as also illustrated in FIG. 2. The housing 11 and the connecting member 15 preferably comprise a single piece of molded plastic. The electrode housing 11 of the carrier 12 has an inner cavity 32 within which the electrode structure 10 is received. A raised portion 17 of the housing 11 provides a lower portion 33 of the cavity 32 within which the proximal end of the plunger 40 is received, as will be described in more detail hereinafter. Slots 34 may be formed in opposite walls of the cavity 32 to receive the guide pins 26 of the electrode structure 10 and thereby ensure proper alignment and simple attachment thereof. Cam surfaces 36 and 38 are formed in the lower part of the cavity 32, for engagement with mating surfaces 29 and 31 of the respective legs 23 and 25 of the electrode body 14, as will be described in greater detail hereinafter. The legs 23 and 25 are received within the connecting member 15 so that the clamping members 16 and 18 are separated while the electrode structure 10 is stored in the carrier 12.

Housed within the carrier 12 is a plunger 40 for moving the electrode structure 10 so that the mating surfaces 29 and 31 thereof move from their positions within the connecting member 15 onto the cam surfaces 36 and 38 for ejecting the electrode structure 10 from the carrier 12 and allowing the electrode structure 10 to attach to the subject. The plunger 40 comprises a flexible tube portion 42, part of which is shown in FIG. 2, and an end portion 46 having a flat, rectangular end adjacent the electrode structure 10. The tube portion 42 is sufficiently smaller in diameter than the inside of the tube 13 to permit the electrode wires 22 and 24 to pass easily therethrough. The flat, rectangular end of the end portion 46 allows steady, even pressure to be exerted against the electrode structure 10 in a manner to be described in greater detail hereinafter. When the plunger 40 is forced against the electrode structure 10 in this manner, the end portion 46 thereof is received within the lower portion 33 of the cavity 32 formed in the raised portion 17 of the housing 11.

Figure 4:
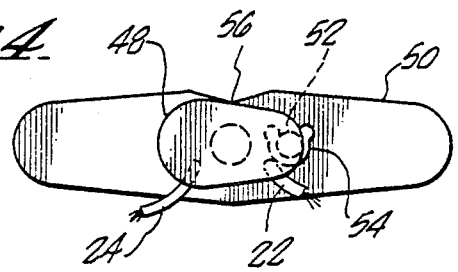
FIG. 4 is a plan view of the end portion of a carrier according to the present invention opposite the end housing the electrode structure, prior to attachment of the electrode structure.
Figure 5:
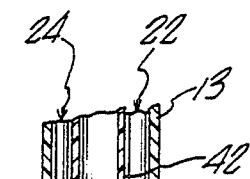
FIG. 5 is a plan view as in FIG. 4 illustrating the end portion of the carrier in readiness for attachment of the electrode structure.
Figure 6:
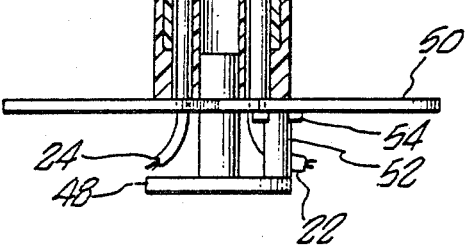
FIG. 6 is a side view, in partial cross section, of the end portion of the carrier shown in FIGS. 4 and 5.

Referring to FIGS. 4, 5 and 6, at the end of the tube 13 opposite the housing 11 there is provided an actuator for operating the plunger 40. Into the end of the flexible tube portion 42 of the plunger 40 there is securely fitted a pressure plate 48. A base 50 is substantially parallel to the pressure plate 48 and is securely mated to the tube 13. For storage prior to use, a guard pin 52 affixed to the pressure plate 48 is inserted into a friction snap retainer or locator 54 in the base 50 as shown in FIGS. 4 and 6. A cutout 56 is provided in the base 50 for receiving the guard pin 52 when the plunger 40 is to be operated as shown in FIG. 5. The pressure plate 48 is preferably asymmetrically shaped to permit ease of operation and certainty of positioning. The U-shaped design of the snap retainer 54 permits rotation of the pressure plate 48 only in the desired direction, as will be more fully explained below.

The electrode structure 10 is attached to the subject to be monitored in the following manner. The carrier 12 containing the recessed electrode structure 10 is positioned with the electrode housing 11 against the area of the skin surface to which the electrode structure 10 is to be attached. If the electrode structure 10 is to be attached to a fetus for heart rate monitoring during labor and delivery, for example, the carrier 12 is inserted into the uterus until the housing 11 contacts the head of the fetus. The physician prepares for attachment of the electrode structure 10 by rotating the plate 48 until the guard pin 52 is removed from the retainer 54, and then further rotating the plate 48 and the flexible tube portion 42 of the plunger 40 fitted thereto approximately 90° to a point where the guard pin 52 is received within the cutout 56 in the base 50. The flexible tube portion 42 of the plunger 40 possesses sufficient rotational flexibility to be rotatable approximately 90° while the end portion 46 of the plunger 40 adjacent the electrode structure 10 remains rotationally fixed within the lower portion 33 of the cavity 32 in the electrode housing 11. The physician then operates the plunger 40 in a manner substantially similar to the operation of a hypodermic syringe, by exerting thumb pressure on the pressure plate 48 and an opposite pressure with two fingers on the base 50. The flat rectangular end of the end portion 46 of the plunger 40 is thereby forced against the closed legs 23 and 25 of the electrode structure 10, causing the electrode structure 10 to be partially ejected from the housing 11. As the electrode structure 10 moves toward the open end of the housing 11, the mating surfaces 29 and 31 on the legs 23 and 25 engage the cam surfaces 36 and 38 of the housing 11, allowing the spring 20 to expand and exert outward force on the legs 23 and 25. The cam surfaces 36 and 38, aided by the expansive force of the spring 20 on the legs 23 and 25, then eject the electrode structure 10 from the housing 11 to the position illustrated in FIG. 3 without the application of further pressure by the plunger 40. For this purpose the cam surfaces 36 and 38 preferably comprise a self-lubricating material. In the position of FIG. 3 the clamping members 16 and 18 are forced together by the spring 20, thus piercing and clamping the epidermic of the subject. Once the members 16 and 18 are clamped onto the subject, the carrier 12 may be removed completely, leaving only the electrode structure 10 with its associated wires 22 and 24. The distal ends of the wires 22 and 24 then may be connected to suitable monitoring equipment (not shown). When monitoring is no longer needed, as after delivery in the case of fetal monitoring, the electrode structure 10 is easily removed by manually compressing the legs 23 and 25 and thus forcing the clamping members 16 and 18 apart.

The body 14 of the electrode structure 10 according to the embodiment described above is preferably constructed by injection molding of a flexible plastic material of the same type used for the housing 11, described below. The clamping members 16 and 18 are approximately 0.01 inch (0.254 mm) to 0.02 inch (0.508 mm) in diameter and are preferably of polished stainless steel, as is the spring. The wires 22 and 24 are insulated copper wire of approximately 18 to 20 gauge.

The electrode structure 10 according to the preferred embodiment measures approximately ⅝" by ⅜" (1.59 cm×0.95 cm) with the clamping members 16 and 18 protruding from the body approximately ⅛" (3.18 mm).

The housing 11 of the electrode carrier 12 is made of any suitable medically approved plastic of self-lubricating quality, and is preferably acetal resin but may be nylon or the like. The housing 11 is sized sufficiently larger than the electrode structure 10 to house the electrode structure 10 adequately. The tube portion 13 of the carrier 12 is made of a flexible or curved plastic or similar material such as linear polyethylene or nylon, and is approximately 11" (27.9 cm) long and 5/16" (7.94 mm) in diameter. The cylindrical connecting member 15 between the housing 11 and the tube 13 is part of the housing molding.

FIGS. 7–10 illustrate a presently preferred embodiment of the electrode and carrier assembly of the present invention. Referring first to FIG. 7, there is illustrated in perspective a portion of an electrode carrier 110 similar to the electrode carrier 12 illustrated in FIG. 1. Within a cavity 112 of an electrode housing portion 114 of the carrier 110 there is housed an electrode structure similar to that described above, the tips of whose clamping portions 116 and 118 are visible in FIG. 7. The carrier 110 also includes a flexible or curved tube portion 120 extending from a cylindrical connecting member 122 and housing a tube 124 and twisted wires 126 and 128. Raised portions 130 on either side of the electrode housing 114 provide channels 132 within the cavity 112 for proper alignment of the electrode, in a manner to be described in more detail hereinafter.

Referring next to FIG. 8, there is illustrated a side cross sectional view of the electrode carrier 110 of FIG. 7, taken along the line 8—8 of FIG. 7. An electrode structure designated generally as 134 is housed in the cavity 112 formed therein and is shown in partial cross section to illustrate its component parts. The general design of the electrode structure 134 is similar to that of the electrode structure 10 previously described. A clip-type body 136 includes arms 138 and 140 supporting opposed clamping members 118 and 116, and further includes legs 146 and 148 joined respectively to the arms 138 and 140, the pairs of arms and legs being connected by a resilient web 150 and the legs 146 and 148 having rounded surfaces 142 and 144 at their outer corners respectively for engaging cam surfaces 143 and 145 within the cavity 112. A spring 152 is embedded in the legs 146 and 148 to exert an outwardly expansive force thereon, urging the clamping members 118 and 116 into a closed position limited by stops 154 and 156. The wire 126 is connected through the leg 148 and the arm 140 to the clamping member 116, and the wire 128 is connected to the spring 152. Guide pins 158 are located on opposite sides of the web 150 for engagement with the slots 132 of the electrode housing 114. The functions performed by this electrode structure are substantially the same as to those previously described in connection with the electrode structure 10.

Also illustrated in FIG. 8 is the tube 124 received within the tube portion 120 of the electrode carrier 110. As illustrated in FIG. 8, the tube 124 is preferably hollow for receiving a connecting pin 160 forming part of a U-shaped plunger 162 which is received within the cylindrical connecting portion 122 of the carrier assembly 110. The tube 124 may be connected to an actuating mechanism similar to that previously described in connection with FIGS. 4–6, whereby pressure may be exerted against the legs 146 and 148 of the electrode structure 134 to partially force the electrode structure 134 out of the carrier 110 in substantially the manner previously described, whereupon the carrier may be removed leaving only the electrode structure 134 and its associated wiring attached to the subject.

Two rounded protrusions 164 and 166 are molded into the proximal end of the electrode housing 114. When the housing 114 is pressed against the subject, such as the scalp of a fetus, these protrusions serve the purpose of gathering a portion of the fetal scalp into the space between the protrusions to provide an easier attachment to the fetal scalp by the clamping members 118 and 116. The depth of penetration of the clamping members into the fetal scalp is thereby more precisely controlled while still providing adequate electrical contact.

Detail of the interior of the electrode carrier 110 and the U-shaped plunger 162 received therein is illustrated in FIGS. 9 and 10, which will be referred to jointly. FIG. 9 is a side cross sectional view taken along the line 9—9 of FIG. 8, and FIG. 10 is an end cross-sectional view taken along the line 10—10 of FIG. 8. It will be observed that the interior of the cylinder connecting portion 122 has a tapered shape for receiving the plunger 162 in the proper orientation. The twisted wires 126 and 128 are received within the U-shaped plunger 162 so that the plunger 162 encounters a minimum of drag or resistance from the wires 126 and 128 upon removal of the plunger 162 following attachment of the electrode structure 134 to the fetus. The tapered shape of the interior of the connecting portion 122 permits proper placement of the plunger 162 against the legs 146 and 148 to insure positive pressure for ejecting the electrode structure 134 from the housing 114. It may be desirable in some circumstances to utilize a single dual conductor wire in place of the two twisted wires to further reduce drag or resistance upon withdrawal of the plunger 162.

The design specifications and materials utilized in the preferred embodiment of FIGS. 7–10 are substantially the same as those previously described in connection with the embodiment of FIGS. 1–6.

While alternative embodiments of the present invention have been described, many modifications and variations thereof will be apparent to those skilled in the art, and it is intended to include all such modifications and variations within the scope of the appended claims.

I claim:

1. Apparatus for use in physiological monitoring comprising
   a clip-type electrode structure having a pair of legs separated by a resilient web, each of said legs supporting a clamping member, at least one of said members being of metal to serve as an electrode,
   means for connecting said metal electrode to monitoring equipment,
   spring means acting upon said legs for urging said members together in a clamping fashion,
   carrier means for housing said electrode structure prior to use with the clamping members separated, and
   means for at least partially ejecting said electrode structure from said carrier means to allow said clamping members to be forced together and become attached to a subject when said carrier means is placed against such subject.

2. Apparatus as in claim 1 wherein said ejecting means comprises a pair of cam surfaces in the carrier means for engagement with mating surfaces of said legs.

3. Apparatus as in claim 1 wherein said ejecting means comprises an elongated tube connected to said carrier means, said tube having a plunger extending therethrough for exerting pressure against said electrode structure 4. A fetal monitoring apparatus comprising
   a clip-type electrode structure having a pair of legs separated by a resilient web, each of said legs supporting a clamping member, at least one of said members being of metal to serve as an electrode,
   spring means acting upon said legs for urging said members together in a clamping fashion,
   means for connecting said electrode to monitoring equipment,
   an elongated tube having housing means at one end thereof for receiving said electrode structure, and said housing means including means for keeping said clamping members separated while said electrode structure is housed therein by engaging said legs and thereby compressing said spring means,
   cam means within said housing means for engaging mating surfaces on said legs, and
   a plunger extending through said tube for causing said mating surfaces to engage said cam means, whereby said electrode structure may be at least partially ejected from said housing means and said clamping members may be forced together and become attached to a subject when said housing means is placed against such subject.

5. Apparatus as in claim 1 or 4 wherein said electrode structure further comprises stop means for limiting the range of expansion of said spring means and thereby limiting the degree of clamping of said clamping members.

6. A physiological monitoring electrode structure for association with a carrier having cam surfaces therein, said electrode structure comprising
   a pair of opposed clamping members, at least one of said members being of metal to serve as an electrode,
   a pair of legs, each of said legs supporting a respective one of said members and said legs being separated by a spring which urges said members together, said legs being separated by a resilient web and having mating surfaces for engagement with said cam surfaces whereby said electrode structure may be at least partially ejected from said carrier when said mating surfaces engage with said cam surfaces, and
   means for connecting said electrode to monitoring equipment.

7. Apparatus adapted for use in attaching a physiological monitoring electrode to the skin of a subject comprising
   a substantially cylindrical tube,
   a housing at one end of said tube adapted to receive a physiological monitoring electrode and adapted to be placed against the skin of the subject,
   a plunger extending through said tube for exerting pressure on the electrode to eject the electrode from the housing, and
   a pair of protrusions extending from said housing for gathering the skin of a subject therebetween when said housing is placed against the subject to facilitate secure attachment of an electrode to the gathered skin when the electrode is ejected from the housing.

8. A fetal monitoring apparatus comprising
   a clip-type electrode structure having a pair of legs separated by a resilient web, each of said legs supporting a clamping member, at least one of said members being of metal to serve as an electrode,
   spring means acting upon said legs for urging said members together in a clamping fashion,
   means for connecting said electrode to monitoring equipment, an elongated tube have housing means at one end thereof for receiving said electrode structure, and said housing means including means for keeping said clamping members separated while said electrode structure is housed therein by engaging said legs and thereby compressing said spring means, cam means within said housing means for engaging mating surfaces on said legs, a plunger extending through said tube for engaging said electrode structure and for causing said electrode structure to engage said cam means upon the application of pressure against said plunger, whereby said electrode structure may be at least partially ejected from said housing means and said clamping members may be forced together and thereby become attached to a subject when said housing means is placed against such subject, and means mounted upon said housing means for gathering the skin of the subject against whom said housing means may be placed and thereby facilitating the secure attachment of said clamping members thereto.

9. A physiological monitoring electrode structure for association with a carrier having cam surfaces therein, said electrode structure comprising a pair of opposed sharpened wires mounted upon arm members, each arm member being connected to a respective leg member, said pairs of arm and leg members being joined by a resilient web, and said leg members being connected by a spring which urges said sharpened wires together, said leg members having mating surfaces for engagement with said cam surfaces whereby said electrode structure may be at least partially ejected from said carrier when said mating surfaces engage with said cam surfaces, and said electrode structure including means for connecting at least one of said sharpened wires to monitoring equipment.

* * * * *